(12) United States Patent
Polak et al.

(10) Patent No.: US 7,521,019 B2
(45) Date of Patent: *Apr. 21, 2009

(54) SENSOR DEVICE AND METHODS FOR MANUFACTURE

(75) Inventors: Anthony J. Polak, Lake Zurich, IL (US); Ralph Ballerstadt, Palatine, IL (US); Allyson Beuhler, Downers Grove, IL (US); Claudia Gamboa, Chicago, IL (US)

(73) Assignee: Lifescan, Inc., Milpitas, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 09/832,663

(22) Filed: Apr. 11, 2001

(65) Prior Publication Data

US 2002/0182658 A1    Dec. 5, 2002

(51) Int. Cl.
*G01N 21/01* (2006.01)
(52) U.S. Cl. .................. 422/82.06; 422/82.07; 422/101; 422/102; 435/4; 435/7.1; 435/287.1; 436/20; 436/172
(58) Field of Classification Search ............ 435/5–7.92, 435/287.2; 600/310–7, 342; 422/82–82.06, 422/70, 101, 102; 436/20, 172
See application file for complete search history.

(56) References Cited

U.S. PATENT DOCUMENTS

| | | |
|---|---|---|
| 3,877,784 A | 4/1975 | Lin |
| 4,058,732 A | 11/1977 | Wieder |
| 4,150,295 A | 4/1979 | Wieder |
| 4,344,438 A | 8/1982 | Schultz |
| 4,737,464 A | 4/1988 | McConnell et al. |
| 4,791,310 A | 12/1988 | Honig et al. |
| 4,954,435 A * | 9/1990 | Krauth ........................ 435/7.93 |
| 5,001,054 A | 3/1991 | Wagner |
| 5,061,076 A | 10/1991 | Hurley |
| 5,143,066 A | 9/1992 | Komives et al. |
| 5,156,972 A | 10/1992 | Issachar |
| 5,232,712 A * | 8/1993 | Mills et al. ................ 425/133.1 |
| 5,342,789 A | 8/1994 | Chick et al. |
| 5,418,154 A * | 5/1995 | Aebischer et al. ............ 435/182 |
| 5,464,438 A * | 11/1995 | Menaker .................... 623/1.43 |
| 5,496,997 A | 3/1996 | Pope |
| 5,605,152 A | 2/1997 | Slate et al. |
| 5,660,848 A | 8/1997 | Moo-Young |
| 5,756,115 A | 5/1998 | Moo-Young |
| 5,773,286 A * | 6/1998 | Dionne et al. ............ 435/297.1 |
| 5,814,449 A | 9/1998 | Schultz et al. |

(Continued)

FOREIGN PATENT DOCUMENTS

EP    0761159 A3    3/1998

(Continued)

OTHER PUBLICATIONS

Kumar et al, Improved double immunofluorescence for confocal laser scanning microscopy, 1999, J Hist Cyt, 47(9), 1213-1217.*

(Continued)

*Primary Examiner*—Nelson Yang

(57) ABSTRACT

The present invention provides a device and methods for detecting the presence of an analyte in a sample using an encapsulated sensor. Methods for manufacturing the sensor are also disclosed.

39 Claims, 2 Drawing Sheets

U.S. PATENT DOCUMENTS

| | | | |
|---|---|---|---|
| 5,864,397 | A * | 1/1999 | Vo-Dinh .................... 356/301 |
| 5,871,628 | A | 2/1999 | Dabiri et al. |
| 5,990,479 | A | 11/1999 | Weiss |
| 5,995,860 | A | 11/1999 | Sun et al. |
| 6,002,954 | A | 12/1999 | Van Antwerp et al. |
| 6,011,984 | A | 1/2000 | Van Antwerp et al. |
| 6,040,194 | A | 3/2000 | Chick et al. |
| 6,049,727 | A | 4/2000 | Crothall |
| 6,081,736 | A | 6/2000 | Colvin et al. |
| 6,110,630 | A | 8/2000 | Reddy et al. |
| 6,114,038 | A | 9/2000 | Castro et al. |
| 6,114,350 | A | 9/2000 | Randall et al. |
| 6,121,075 | A | 9/2000 | Yamashita |
| 6,123,700 | A * | 9/2000 | Mills et al. .............. 604/890.1 |
| 6,134,461 | A | 10/2000 | Say et al. |
| 6,163,714 | A | 12/2000 | Stanley et al. |
| 6,177,684 | B1 | 1/2001 | Sugiyama |
| 6,232,130 | B1 | 5/2001 | Wolf |
| 6,251,303 | B1 | 6/2001 | Bawendi et al. |
| 6,256,522 | B1 * | 7/2001 | Schultz ...................... 600/317 |
| 6,274,323 | B1 * | 8/2001 | Bruchez et al. ................ 435/6 |
| 6,379,622 | B1 | 4/2002 | Polak et al. |
| 6,454,710 | B1 | 9/2002 | Ballerstadt et al. |
| 6,531,581 | B1 * | 3/2003 | Nardone et al. ............ 534/560 |
| 6,678,564 | B2 * | 1/2004 | Ketterl et al. ............... 607/137 |
| 6,844,166 | B1 | 1/2005 | Wolf |
| 2004/0157951 | A1 | 8/2004 | Wolf |

FOREIGN PATENT DOCUMENTS

| EP | 0761159 B1 | 3/1998 |
|---|---|---|
| WO | WO 00/20862 | 4/2000 |

OTHER PUBLICATIONS

Tolosa et al, optical assay for glucose based on the luminescnence decay time of the long wavelength dye Cy5, 1997, Sensors and Actuators, B45, 93-99.*

Berlier et al, Quantitative comparison of long-wavelength alexa fluor dyes to cy dyes: fluorescence of the dyes and their bioconjugates, 2003, 51(12), 1699-1712.*

Panchuk-Voloshina et al, Alexa Dyes, a series of new fluorescent dyes that yield exceptionally bright, photostable conjugates, 1999, J Hist Cytochem, 47(9), 1179-1188.*

Ferri et al, Direct eye visualization of Cfluorescence for immunocytochemistry and in situ hybridization, 2000, J Hist Cytochem, 48(3), 437-444.*

Sohrab Mansouri and Jerome S. Schultz, "A Miniature Optical Glucose Sensor Based On Affinity Binding", Biotechnology, 1984, pp. 885-890.

W. Rudolf Seitz, "Optical Sensors Based In Immobilized Reagents", Biosensors Fundamentals and Applications, Oxford University Press, copyright 1987, pp. 599-603.

D. L. Meadows and J. S. Schultz, "Design, Manufacture and Characterization of an Optical Fiber Glucose Affinity Sensor Based on An Homogeneous Fluorescence Energy Transfer Assay System", Analytica Chimica Acta 280, 1993, pp. 21-30.

Klaus Mosbach and Olof Ramström, "The Emerging Technique of Molecular Imprinting and Its Future on Biotechnology", Bio/Technogoly vol. 14, 1996, pp. 163-170.

Margaret A. Hines et al., Synthesis and Characterization of Strongly Liminescing ZnS-Capped CdSe Nanocrystals, J. Phys. Chem., 100, 1996, pp. 468-471.

Dmitri Ivnitski et al., "Biosensors for Detection of Pathogenic Bacteria", Biosensors and Bioelectronics 14, 1999, pp. 599-624.

Ryan J. Russell et al., "A Flourescense-Based Glucose Biosensor Using Concanavalin A and Dextran Encapsulated In A Poly(ethylene glycol) Hydrogel", Analytical Chemistry Vo. 71, No. 15, 1999, pp. 3126-3132.

M. Dittrich et al., "Branched Oligoester Microspheres Fabricated By A Rapid Emulsion Solvent Extraction Method", J. Microencapsulation, vol. 17, No. 5, 2000, pp. 587-598.

J. Molpeceres et al., "Biodegradable Nanoparticles As A Delivery System For Cyclosporine: Preparation and Characterization", J. Microencapsulation, vol. 17, No. 5, 2000, pp. 599-614.

Ralph Ballerstadt and Jerome S. Schultz, "A Fluorescence Affinity Hollow Fiber Sensor For Continuous Transdermal Glucose Monitoring", Analytical Chemistry vol. 72 No. 17, 2000, pp. 4185-4192.

The Nut Factory: Kitchen: Interesting Facts: Chocolate Panning:, "Panning Nuts in Chocolate", <http://www.the_nutfactory.com/kitchen/facts/facts-chocolate-panning.html>, Mar. 16, 2001, pp. 1-4.

John Franjione, Ph. D. et al.—Technology Today—Art & Science Microencapsulation, "The Art and Science of Microencapsulation", <http://www.swri.org/3pubs/ttoday/summer/microeng.htm>, Mar. 16, 2002, pp. 1-7.

* cited by examiner

SENSOR DEVICE AND METHODS FOR MANUFACTURE

BACKGROUND OF THE INVENTION

The present invention provides a device and methods for detecting the presence of an analyte in a sample, more particularly to devices and methods for transdermal monitoring of an analyte. Methods for manufacturing the device are also disclosed.

The monitoring of certain analyte concentrations in the body enables early detection of health risks, and identifies the need for the introduction of therapeutic measures. One of the most commonly monitored analytes is glucose. The concentration of glucose in the blood is an important parameter which determines the appropriate dosages of insulin for diabetics. Various methods have been developed for monitoring glucose levels in the blood, including methods conducted in vivo. For example, an implantable fluorescence affinity hollow fiber sensor has been reported for the continuous transdermal monitoring of glucose in the blood (see, for example, Schultz et al., *Analytical Chemistry* Vol. 72, No. 17, pp. 4185-4192). The interiors of such hollow fiber sensors are packed with cross-linked dextran beads and fluorescently-tagged bio-reagents that display fluorescence changes with rising concentrations of glucose. Detection of the fluorescence is achieved extracorporeally (e.g., with an optical unit incorporating a laser and a photodetector) and is correlated with a concentration of glucose in the blood.

Implantable sensors currently require some form of surgery to place the implant under the skin because of the large size of the implant. The larger the implant, and the more exterior seams and sealing interfaces it has, the more likely that there will be an immunological response or infection. Infection is especially problematic for immuno-compromised patients or patients receiving immunosuppressive drugs.

In addition to undesirable immunological response, current implantable sensors lack long-term usefulness due to potential leakage and rupture at the assembly seams. Whether the device is assembled with mechanical O-rings or chemical adhesives, the seams are prone to failure in the liquid environment of a living organism. An example of a sensor requiring an O-ring seal is disclosed in U.S. Pat. No. 5,143,066. Other implantable devices, such as those disclosed in U.S. Pat. Nos. 5,756,115 and 5,814,449, rely on adhesives to seal their layers or ends together. Current implants generally consist of a tube or hollow fiber sealed at both ends with an adhesive. Accordingly, there is a need to develop implantable sensor devices that lack sealing surfaces and can be made in a wide variety of sizes, starting in the sub-micron range.

This invention provides an encapsulated, size-scalable sensor device that can be made small enough to implant with only a small incision or, more preferably, with a needle. If desired, multiple devices can be implanted at one site to increase the signal strength. Additionally, the encapsulation membrane is "seamless" in that it forms a contiguous surrounding for the device that lacks joining seams or edges.

Unlike mechanically sealed devices which rely on rubber-type O-rings or adhesives to seal their parts together, the present device lacks edges or sealing interfaces. This elimination of joining seams or edges provides enhanced rupture resistance and decreased chance of immunological response. Additionally, the smooth exterior aids in ease of implantation. The device is also significantly easier to manufacture because the various components do not require manual assembly and sealing.

BRIEF SUMMARY OF THE INVENTION

The device of the present invention has one or more of the following advantages: it is very strong and resistant to rupture or leakage; it can be sufficiently small in size, into the sub-micron range, to allow it to be implanted under the skin following a small incision; the small size and smooth exterior of the device reduce the chance of immunological response; and hundreds or even thousands of these devices to be inserted at one site with a needle (making this an out patient process) or embedded in a resin to form a non-invasive patch, which could be located on the outside of the skin and could sample the interstitial fluid through microdialysis or an electrical current method.

DETAILED DESCRIPTION OF THE INVENTION

Figure 1:
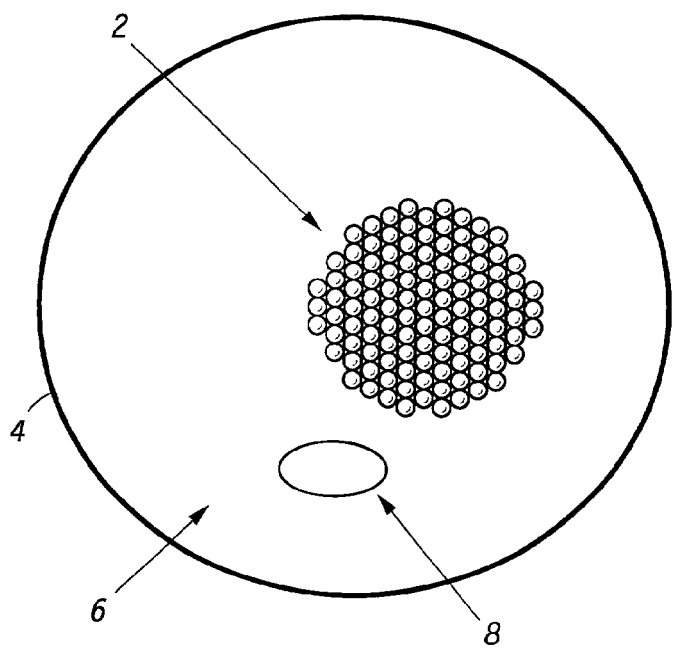
FIG. 1 illustrates an analyte-sensing device in accordance with an embodiment of the present invention having binding substrate layer (2), analyte-permeable membrane (4), void volume (6), and reference (8).

The devices and methods for monitoring an analyte in accord with the present invention are based on a competitive reaction for a binding site of the binding substrate between the analyte of interest and a fluorescently labeled analogue. At low concentrations of analyte, the labeled analogue binds to the binding substrate. As the concentration of analyte increases, the labeled analogue dissociates from the binding substrate. The binding substrate absorbs a majority of the excitation and emission wavelengths of the fluorescent label (e.g., by the action of a dye attached to the binding substrate), such that in the presence of light corresponding to the excitation wavelength, minimum fluorescence is generated when the labeled analogue resides within the substrate (i.e., when the concentration of analyte is low). Contrariwise, increased fluorescence is detected when the labeled analogue resides outside the binding substrate (i.e., when the concentration of analyte is high). By measuring the fluorescence over a range of analyte concentrations, a correlation can be established between the magnitude of a fluorescence signal and the concentration of analyte giving rise to the signal.

The device includes components encapsulated within a seamless analyte-permeable membrane, which is mostly transparent to the excitation wavelength of the fluorescent label. The components include: (a) a binding substrate that has at least one affinity binding site for the analyte; (b) at least one analogue that binds in the binding site and that has a label with a first emission wavelength; (c) a quenching dye; and (d) a void volume. The device can also include a reference.

The ability to construct implantable sensor devices without sealing interfaces provides many advantages. Because interfaces are known to exhibit the highest levels of stress in a structure, seamed devices are prone to failure at their sealing surfaces. Not only are the seams continuously exposed to water, but they must be able to withstand flexion and impact stresses both within the body and during implantation. In a similar manner to the shell of an egg, which is very thin but very strong due to its lack of seam interfaces, so are the present devices.

In addition to strength, the seamless nature of the present devices provide no rough edges or other crevices for proteins and other biological molecules to adhere. This allows for the devices to produce little irritation and minimal side effects after implantation. The smooth exterior also aids in ease of implantation and explantation.

Another significant benefit of the present invention is the ability to control the void volume by non-mechanical means. In the present devices, the ratio of void volume to core volume is determined by the volume of an intermediate layer. By adjusting the amount of intermediate material applied to the core, the ratio of the volume of the intermediate layer to core volume is controlled.

Device

The device can range in size from about 50 nm to about 5 cm, preferably 50 microns to 1 cm, and most preferably 100 microns to 5 mm. Devices of 150 microns and larger may be used to prevent the devices from leaching out of the interstitial tissues and entering the blood stream. In addition, devices 10 microns and smaller are in the same size range as tattoo inks and may be implanted just under the surface of the skin. To generate sufficient fluorescence for detection, a singular large device, or a plurality of smaller devices may be used. If micron range beads are used, it is foreseeable that thousands may be injected under the skin.

Although the devices may be any shape, spray-drying, solvent-evaporation, and dip-coating methods tend to produce nearly spherical or elliptical devices. Additionally, if the core components are spray-dried onto a release sheet, the devices are ellipses with one dimension being larger than the others. When a film-format synthesis is used, the device is basically flat, even though multiple elliptical cores or a single flat core is encapsulated. Such film-format devices may be made individually or as a single sheet and cut into the desired shape.

Analyte

"Analyte" refers to one or a plurality of species having a concentration of interest.

The nature of the analyte monitored in accord with the present invention is unrestricted, provided the analogue and the binding substrate are appropriately matched therewith to ensure competitive binding reaction between the analogue and the analyte or analogue and substrate. Preferred analytes include but are not limited to glucose, coumadin, synthroid, cyclosporin, erythropoietin, lopid, monopril, digoxin, amiodarone, prothrombin, cytokines, chemokines, creatinine, lactate, and various chemotherapeutic drugs, such as taxol, fluorouracil, and vincristine. The present invention can be adapted for simultaneous monitoring of multiple analytes by including substrates and analogues matched to each of the analytes of interest.

Labeled Analogue

"Analogue" refers to one or a plurality of ligands that binds to the substrate at low analyte concentrations, and dissociates from the binding substrate as the concentration of analyte increases. Suitable analogues include, but are not limited to dextran, lectins, Concanavalin-A, wheat germ agglutinin, soybean agglutinin, and glycogens, yeast mannans, amylopectins, levans, globulin, proteins, hormones, antibodies, thyroxin binding globulin, actin, and tubulin. "Labeled analogue" refers to an analogue that is fluorescently labeled.

In the absence of analyte, labeled analogues mostly reside within the pores of the binding substrate. The labeled analogues affinity bind to this binding substrate, but can also affinity bind to the analyte. When analyte flows into the device, it displaces labeled analogues from the binding substrate. Following displacement, the labeled analogues migrate to the void volume, at which point their emission wavelength can be detected upon excitation. As the concentration of analyte increases within the analyte-permeable membrane, a greater percentage of the labeled analogues reside in the void volume; thereby increasing the intensity of label emission.

In certain embodiments, the labeled analogue can also bind, by affinity binding, to the analyte in addition to binding to the binding substrate. The labeled analogue can be any molecule that is too large to pass through the analyte-permeable membrane, but small enough to enter the pores of the binding substrate and affinity bind to the analyte or binding substrate.

Attached to the analogue by a covalent bond or other means is a fluorescent label. When irradiated with an appropriate excitation wavelength, the label emits light at a first wavelength that may be detected outside of the body. Although the excitation wavelength is preferably generated by a visible or infrared laser, any suitable electromagnetic radiation from X-ray to infrared may be used. Light and electromagnetic radiation from X-ray to infrared are synonymous as used herein.

The fluorescent label can be any label that fluoresces when irradiated, such as organic dyes or quantum dots. A broad variety of fluorescent label dyes are known in the art and are commercially available, for example, from Molecular Probes and Amersham Pharmacia Biotech.

Suitable fluorescent labels include those sold under the tradename ALEXA FLUOR®. These labels are dyes with trade secret compositions which may be purchased from Molecular Probes, Inc. (849 Pitchford Avenue, Eugene, Oreg. 97402-9165 USA). Other suitable labels include the cyanine dyes prepared with succinimidyl ester reactive groups, such as Cy-5 and Cy-5.5. The number immediately after the "Cy" indicates the number of bridge carbons. The number following the decimal point indicated a unique dye structure, which is determined by the substituents on the structure. Cy-5 and Cy-5.5 are available from Amersham Pharmacia Biotech (Piscataway, N.J., USA).

Especially preferred dyes include the ALEXA FLUOR® dyes, especially ALEXA 633, which has an excitation wavelength of 633 nm, and an emission wavelength of 647 nm.

Binding Substrate

"Substrate" or "binding substrate" refers to one or a plurality of receptors having at least one binding site and, more preferably, having a plurality of binding sites.

In preferred embodiments, the binding substrate has a large surface area containing multiple binding sites. More preferably, the binding substrate has a plurality of pores having a porosity sufficiently large to permit ingress and egress of the labeled analogue. The binding substrate may inherently provide a binding site for the analyte, or a molecule may be attached to the binding substrate to create a binding site. Suitable porous materials for use as binding substrates include, but are not limited to, dextran, cross-linked dextran beads (such as SEPHADEX), agarose, SEPHAROSE, ceramic, alumina, polymers, silica, glycogens, yeast mannans, amylopectins, levans, globulin, proteins, hormones, antibodies, thyroxin binding globulin, actin, and tubulin. For glucose sensors, the preferably binding substrate is cross-linked dextran beads having a plurality of binding sites within the pores.

For embodiments requiring glucose binding sites, such sites are already provided by the glucose termini of the cross-linked dextran bead. For embodiments utilizing binding sites other than glucose, the desired binding sites can be introduced into the beads by the modification procedures described below.

Preferably, the binding substrate has a diameter ranging from about 50 to 500 microns, and more preferably from about 10 to 50 microns. Most preferably, the binding substrate has a diameter of about 25 microns.

Binder

If a larger or immobilized binding substrate is desired, for example to make a binding substrate in the form of a thin film, multiple substrate particles may be combined with a binder. The binder must be porous enough to allow labeled analogues to pass from the binding substrate to the void volume and be compatible with the other sensor components.

Suitable binders include hydrogels, silicon containing polymers, polyvinyl alcohols, polysulphones, cross-linked polyacrylamides, epoxies, polyesters, polymethyl methacrylate, polyurethanes, polycarbonates and other permeable polymers known to those of skill in the art. Generally, useful binders have a molecular weight from 10,000 to 500,000. When SEPHADEX and ALEXA 633 labeled Concanavalin-A are used in a glucose sensing device, the preferred binding material is cross-linked polyacrylamide, available from HT Photopolymers AG (Basel, Switzerland).

Dye

Suitable dyes in accordance with the present invention have a broad absorption spectrum that overlaps the fluorescence excitation and emission spectra of the fluorescent label, thereby minimizing fluorescence detection from the fluorescent label. In such instances, the dyed binding substrate provides a "light-blocking" or a "light quenching" substrate that minimizes or prevents fluorescence detection from the labeled analogue when the concentration of analyte is low.

Preferred dyes include, but are not limited to, Alkali Blue 6B, Azure A, Evans Blue (also called Direct blue 53), and Celestine blue (also called Mordant blue 14). Preferably, the dye is Alkali Blue 6B, which has a broad absorption spectrum from about 500 nm to about 700 nm. Other useful quenching-dyes include Safranin and Pararosaniline.

The dye is linked to the binding substrate, either physically or chemically. Preferably, the dye is covalently linked to the binding substrate. Preferably, the dye is attached to the binding substrate by means of a bifunctional linker. More preferably, the dye is attached using the DVS (i.e., divinyl sulfone) method, as described in *Analytical Chemistry*, Vol. 72, No. 17, p. 4186.

Preferably, the binding substrate contains about 0.5 to 5 micromoles of dye per mL of a wet suspension of binding substrate. More preferably, the binding substrate contains about 1 to 3 micromoles of dye per mL. Still more preferably, the binding substrate contains about 2 to 3 micromoles of dye per mL.

In embodiments where the analyte of interest is glucose, and the labeled analogue is Concanavalin-A labeled with ALEXA633, a preferred dye for the binding substrate is Alkali Blue 6B.

A dye, such as Alkali Blue, may also be attached to the binder. For example, the dye may be attached to a co-polymer of polyacrylamide and glycidyl methacrylate by reacting the primary amide substituent on the Alkali Blue dye with the epoxide group of the glycidyl methacrylate.

Reference

The reference absorbs at an excitation wavelength and emits at a second wavelength which is different from that emitted by the labeled analogue. To prevent the need for multiple excitation sources, it is advantageous that the reference and analyte label absorb at the same wavelength.

Unlike the intensity from the labeled analogue, the intensity of the reference is invariant; it does not vary with analyte concentration. The intensity of the reference emission may be compared to the intensity of the labeled analogue to determine the analyte concentration.

Although not necessary, the present device incorporates the reference in close proximity to the labeled analogue, which allows for simultaneous cancellation of intensity fluctuations that would otherwise result in analyte concentration errors. Such fluctuations include source intensity variation, the position and distance of the source in relation to the device, and skin pigmentation. Because the concentration of the analyte is determined by comparing the reference and labeled analogue emissions, locating the reference in close proximity to the label increases accuracy of the device.

In addition to greater accuracy, when the reference shares the environment of the labeled analogue, its invariant nature may be used to locate the device under the skin. By maximizing the intensity of the reference emission received while moving the excitation source/detector above the skin, the device is accurately aligned with the source/detector. Greater alignment precision reduces the need for a larger implanted device.

The reference may be placed in any location where its concentration in the device remains constant. It is preferably placed in the void volume, physically or chemically attached to the binding substrate or analyte-permeable membrane, or incorporated into the analyte-permeable membrane. If it is in contact with the analyte permeable membrane, it must be impermeable to the membrane so it does not leach out.

The reference can be an organic dye or a quantum dot. Suitable reference dyes for use in accord with the present invention include but are not limited to: TRACER DYE (Molecular Probes, 4849 Pitchford Avenue, Eugene, Oreg., 97402-9165) and phycobiliproteins (PBXL3, Martek Biosciences, Corp., Columbia, Md.). TRACER DYES are ultra-clean polystyrene microspheres loaded with proprietary dye agents. Other dyes include the previously mentioned cyanine dyes, such as Cy-5 and Cy-5.5.

Alternatively, the reference can be a quantum dot. Quantum dot particles measure only a few nanometers in diameter and come in a nearly unlimited palette of colors. They can be linked to other molecules (such as bio-molecules, including proteins and polynucleotides, glass, and plastic) to adjust their solubility and form "quantum dots." The emission wavelength of quantum dots can be varied by varying the size of the nanoparticles and can be excited with white light or a single-color laser. Furthermore, the quantum dots have increased photostability than traditional organic reference dyes, which photobleach after continued irradiation by a laser.

The molar ratio of reference fluorochromes to labeled analogue fluorochromes is preferably from about 0.005 to 2, most preferably from about 0.01 to 1 molar units.

Analyte-Permeable Membrane

The analyte-permeable membrane or shell encloses the components of the device and allows the analyte to enter and exit the device while trapping the device components. That is, the membrane of the present invention can be made of any material impermeable to the labeled analogue but permeable to the analyte. The membrane is preferably comprised of a biocompatible material.

Suitable materials for the analyte-permeable membrane include natural and synthetic polymers having pore sizes through which the analyte will pass, the device components will not pass, and that are mostly transparent to the irradiation light. The membrane material is typically insoluble in the interstitial fluid but allows free diffusion of analyte and interstitial fluid in and out of the device capsule.

Suitable materials include, but are not limited to, cellulose acetate, polysulfones, silicones, fluorosiloxanes, acrylics, cellulose, cellulose esters (such as cellulose acetate and cellulose triacetate), cellulose nitrate, cross-linked poly(hydroxy ethyl methacrylate), such as (polyethoxy (5) methacrylate (HEMA5) and polyethoxy (10) methacrylate (HEMA10)), cross-linked poly(vinylpyrrolidone), cross-linked polyacrylamide, ethylene vinyl acetate copolymers, glutaraldehyde, hydrogels, poly(benzimidazoles), poly(urethanes), poly(vinyl chlorides), poly(vinylidene) fluoride, polyamides, and polycarbonates and mixtures thereof.

Preferred analyte-permeable membranes are composed of cellulose acetate or polysulfone. Most preferred are cellulose acetate membranes having a molecular cutoff of 10 kDa.

The membrane can optionally contain other components, such as references and magnetic or metallic particles that can be used to locate the sensor after implantation. Optionally, the analyte-permeable membrane may be treated with a biocompatibility enhancer, including polyethylene glycol, polysilicones, parylene, or angiogenic materials, such as basic fibroblast growth factor-bFGF.

The thickness of the membrane is preferably between about 10 to 200 microns. More preferably, the thickness is between about 15 to 100 microns. Still more preferably, the thickness is about 20 microns.

For embodiments in which the analyte of interest is glucose, cellulose acetate is preferred. When the labeled analogue is fluorescently labeled Concanavalin-A, the membrane typically has a molecular weight cutoff of about 10 kDa. When the analogue is fluorescently labeled dextran, the membrane typically also has a molecular weight cutoff of about 10 kDa.

Void Volume

Analyte, labeled analogue and water can occupy the void volume. If a reference is in the void volume, it may also move freely about. Controlling the ratio of the void volume to the volume of the binding substrate allows optimization of the intensity of the light emitted from the fluorescent label.

Figure 2:
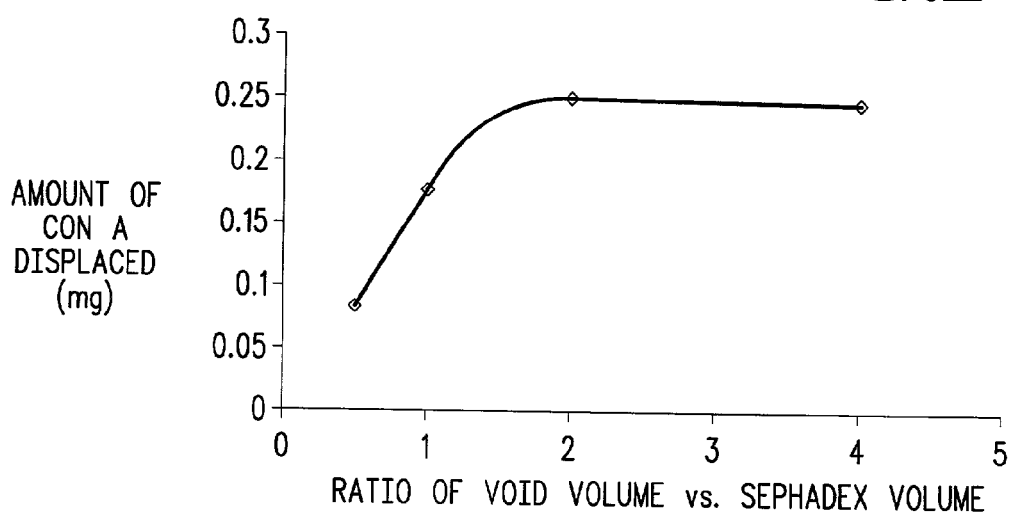
FIG. 2 illustrates the amount of labeled Concanavalin-A displaced from the SEPHADEX core (which is proportional to fluorescent signal intensity) and the ratio of void volume to volume occupied by the core.

This is evident from FIG. 2, which shows the amount of labeled Concanavalin-A (Con-A) displaced from the light-quenching binding substrate (which is proportional to fluorescent signal intensity) and the ratio of void volume to volume occupied by the SEPHADEX core. One can see from FIG. 2 that labeled Concanavalin-A displacement is optimized when the ratio of void volume to SEPHADEX substrate is between about 2:1 and 4:1. While it is optimal to displace as much labeled analogue from the substrate as possible to generate a large fluorescence signal, this is not the only consideration.

TABLE 1

| Volume Ratio Void vs. Substrate | Diffusion Time in Seconds | | Device Response Time Seconds |
|---|---|---|---|
| | Glucose | Con-A | |
| 0.5 | 32 | 9 | 41 |
| 1 | 38 | 35 | 73 |
| 2 | 63 | 143 | 209 |
| 3 | 98 | 321 | 419 |
| 4 | 166 | 892 | 1058 |

As shown above in Table 1, as the ratio of void volume to substrate increases, the response time of the sensor tends to triple as the void volume doubles. Due to these competing effects, the optimal void volume to substrate ratio for the present device is preferably about 0.05 to about 5, more preferably between about 0.5 and about 3, and most preferably about 1.

Because the present devices are optimized for near real-time analyte monitoring, they use a most preferred void volume to substrate ratio of about 1:1 to maximize response time in relation to fluorescence intensity. However, it is foreseen that by adjusting the void volume to substrate ratio a device may be optimized for maximum fluorescence.

The optimum ratio of void volume to binding substrate may be determined for a desired emission intensity or response time by fabricating multiple devices with different ratios of intermediate layer to binding substrate. The fluid nature of the intermediate layer and binding substrate during fabrication allows for precise control of the volume of intermediate layer to binding substrate incorporated into each device. By fabricating a series of devices, each with a different ratio of intermediate layer to binding substrate, a series of devices with different ratios of void volume to binding substrate volume is formed after conditioning. These devices are exposed to the analyte of interest and irradiated with an excitation wavelength. A detection system is used to determine which device produces maximum intensity for a desired response time. Multiple devices with the desired emission intensity in relation to response time may then be fabricated based on the ratio of intermediate layer to binding used for the selected device.

Intermediate Layer

During conditioning, removal of the intermediate layer results in formation of the void volume. The intermediate layer may be a solid, semi-solid, liquid, or a mixture of solid and liquid. Preferably, the intermediate layer is a solid, but can be any material having a molecular size small enough to diffuse out of the analyte-permeable membrane, thereby creating the void volume after device fabrication. Preferable intermediate layer materials are polyethylenes, polyethylene glycol, polyvinyl alcohol, paraffin, plasticizers, oils, glucose derivatives, and mixtures thereof.

If the intermediate layer is a liquid or semi-solid, the viscosity of the liquid or semi-solid and phase separation with the analyte-permeable membrane can determine void volume thickness. When the materials that make up the intermediate layer and core are dispensed as liquids, highly accurate measuring devices, such as micropipettes, may be used to control the void to core volume ratio.

If the intermediate layer is a solid or semi-solid material, controlling its thickness prior to dissolution results in control of the void volume. Such molecular level control of the void volume results in significantly increased control of the void to core volume ratio.

Device Manufacture

Depending on the configuration of the device of the present invention, the device can be manufactured in one of two ways.

In the embodiment where the binding substrate is within the void volume, the binding substrate is first encapsulated with an intermediate layer, thereafter the intermediate layer is encapsulated with an analyte-permeable membrane, and subsequently the device is conditioned to remove the intermediate layer. When the intermediate layer is removed, a void volume is created between the core and the outer analyte-permeable membrane. The binding substrate may further have a molecular imprint of the analyte.

In the embodiment where the void volume in within the binding substrate, the intermediate layer is first encapsulated with a binding substrate, thereafter the binding substrate layer is encapsulated with the analyte-permeable membrane, and subsequently the device is conditioned to remove the intermediate layer. When the intermediate layer is removed, a void volume is created internal to the core.

In other embodiments, the void volume may be defined by the analyte permeable membrane and the binding substrate. This could be accomplished by juxtaposing the binding substrate and intermediate layers and thereafter encapsulating the juxtaposed layers. Following conditioning, the device would have a void volume that was partially surrounded by binding substrate and partially bounded by analyte permeable membrane.

Depending on the application and the analyte-permeable membrane, the encapsulation can be done with or without solvent, by spraying, emulsion, extrusion, dipping, roller-coating, curtain-coating or another conventional process known in the art. One or more of these methods may be used singularly, consecutively, or in combination to produce the devices of the present invention.

Encapsulation of the core components with an intermediate layer is preferably done by a method in which the volume and/or thickness of the layer can be regulated. As the intermediate layer will ultimately become the void volume, it is beneficial to control its volume. The ratio of void volume to binding substrate may be controlled by adjusting the volume of binding substrate material verses volume of intermediate layer material used to make the sensor device. This is precisely done using micropipettes, microemulsions, or other encapsulation techniques known to those of skill in the art.

In roll coating, the core is rolled or stirred in a container as the intermediate layer material and then the material that forms the analyte-permeable membrane are slowly added to the container. A solvent may optionally be used. As these materials are added, the core is coated. The more material added, the heavier and thicker the coating.

In emulsion methods, a solution of the core components and intermediate layer is placed in an organic solvent that contains and solubilizes the analyte-permeable membrane material. The organic solution is then poured into a large excess of deionized water containing an emulsifier and agitated until the organic solvent evaporates. Once the organic solvent is gone, the capsules are collected and conditioned.

In spray drying, a gas (air) is used to suspend the cores while the intermediate layer and analyte-permeable membrane are consecutively applied. First, the intermediate layer is applied as the cores are sprayed into air to dry. The spray drying process is then repeated with a liquid solution of the analyte-permeable membrane. The capsules are collected and conditioned to remove the intermediate layer.

Conditioning

During conditioning, the analyte-permeable membrane becomes more porous (swollen) and the intermediate layer diffuses out of the capsule leaving behind the core and a void volume.

Conditioning can be performed by soaking the device containing the intermediate layer in a liquid that can pass through the analyte-permeable membrane, such as water, for a time sufficient for the intermediate layer to leave the device. The conditioning liquid can be any liquid that is inert to the analyte-permeable membrane and core that will displace or dissolve the intermediate layer.

The conditioning liquid can optionally contain an agent to assist in the degradation of the intermediate layer. For example, emulsifiers can be added to the conditioning liquid to aid in the dispersion of the dissolved material out of the device.

The amount of time sufficient to remove the intermediate layer depends on the material used to form the intermediate layer. Typically, conditioning takes between about 1 and 48 hours, preferably 1 and 24 hours, more preferably 1 and 12 hours.

Implantation of Device

The analyte sensing capsule or capsules making up the device may be implanted under the skin using common surgical methods. Additionally, because the device can consist of a plurality of small capsules, as opposed to one large implant, a hollow needle may be used. A reciprocating hollow needle, similar to that used to inject colored inks under the skin for tattooing, may be used. Because the device may be implanted by needle at a shallow tissue depth, the procedure is much less involved than surgically implanting a larger device.

In addition to being implanted, the analyte sensing capsules may be imbedded in a patch and placed above the skin. Methods known in the art may be used to route interstitial fluid to the patch where it can enter the sensing capsules.

Excitation Sources and Detectors

Many excitation sources which produce light at the absorption wavelengths of the fluorescent label are available. Some possibilities include lasers and LED's. Lasers are preferred when the device is implanted in a human because of their high power, narrow spectral linewidth, and fast response time. A laser emitting between 630 and 1200 nm, inclusive, is preferred since skin is substantially transparent within these wavelengths.

Many detection systems, including photodiodes, avalanche diodes, CCD's, and photomultipliers may be used. In a preferred embodiment the optical sensor described in co-pending U.S. application, Ser. No. 09/832,521, entitled "System Using A Portable Detection Device For Detection of an Analyte Through Body Tissue", filed concurrently with this application, is used.

Calibration of the emission signal of the fluorescent label may be effected by comparing or "ratioing" it to that of the reference. Thus, the fluorescent label and reference may be irradiated with light of a specific wavelength, more than one specific wavelength, or a range of wavelengths, which may or may not be the wavelength of maximum absorption. The fluorescence emission may be measured at specific wavelengths, which may or may not be the wavelength of maximum emission intensity, or a range of wavelengths in conjunction with specific light filtering devices. By this procedure, the fluorescence emission of the fluorescent label may be discerned from that of the reference.

Expressing the emission of the fluorescent label as a fraction of the emission of the reference yields a signal ratio that is sensitive to the analyte of interest and less sensitive to excitation source fluctuations and misalignment of the implant and detector than if a single fluorescent label sensor device were used. In this manner, the amount of analyte can be quantified.

EXAMPLES

The reagents and materials used in the following representative procedures were obtained from the following sources:

| MATERIAL | SUPPLIER |
| --- | --- |
| ALEXA633-Concanavalin-A | Molecular Probes, Eugene, OR, USA |
| Alkali Blue 6B | Sigma, St. Louis, MO, USA |
| Concanavalin-A | Sigma, St. Louis, MO, USA |
| Dimethyl sulfoxide | Aldrich, Milwaukee, WI, USA |
| Divinyl sulphone (DVS) | Sigma, St. Louis, MO, USA |
| Glycine | Sigma, St. Louis, MO, USA |
| Phosphate buffered solution (prepared vials) | Sigma, St. Louis, MO, USA |
| SEPHADEX G-200 (superfine) | Amersham Pharmacia, Piscataway, NJ, USA |
| SEPHAROSE B | Sigma, St. Louis, MO, USA |
| Polyethylene glycol (PEG) | Aldrich, Milwaukee, WI, USA |
| Polyacrylamide | HT Photopolymer, Basel, Switzerland |
| Ethylene glycol | Sigma, St. Louis, MO, USA |
| NaIO$_4$ | Aldrich, Milwaukee, WI, USA |
| 0.01 M sodium carbonate buffer pH 9.2 | Aldrich, Milwaukee, WI, USA |
| Methyl-mannose | Sigma, St. Louis, MO, USA |
| glucose-PITC | Sigma, St. Louis, MO, USA |

*ALEXA633-Concanavalin-A was purified by affinity chromatography before addition to microcapsule solution and quantitated by UV Spectroscopy. In all cases the SEPHADEX/PEG ratio was 1/1 to ensure 1:1 ratio of SEPHADEX core to void volume.

Example 1

Preparation of Cores with Dyed SEPHADEX Substrates and ALEXA633-Concanavalin-A Analogues Dyeing of SEPHADEX Beads For the dyeing procedure the DVS-method previously described by Porath et al. (Porath, J.; Laas, T.; Janson, J.-C. *J. Chromatography,* 1975, 103, 49-62) was applied. SEPHADEX G200 beads were pre-swollen in 20 mL distilled water overnight. The beads were washed over a sieve with several volumes of distilled water. The bead suspension (12 mL) was then mixed with 12 mL of a 1 M sodium carbonate buffer solution (Na$_2$CO$_3$, pH 11.4) in a beaker. The suspension was intensively stirred on a magnetic stirrer for the duration of the procedure. DVS (800 μl) was added to the suspension and the reaction allowed to proceed for 1 hour. The beads were washed over a sieve with copious amounts of distilled water to remove non-bound DVS, and subsequently equilibrated with 0.5 M sodium hydrogen carbonate buffer (NaHCO$_3$, pH 11.4). Alkali Blue 6B (30 mg) was dissolved in DMSO (1 mL). The resultant solution was then slowly added to the stirred suspension and the reaction was allowed to proceed overnight. Then glycine (1 g) was introduced into the mixture to neutralize remaining active DVS groups. After 1 hour, the beads were transferred into a 15 mL plastic vial and centrifuged in order to remove non-bound dye molecules. The supernatant was discarded. The beads were re-suspended in DMSO, shaken, and centrifuged again. This procedure was repeated several times until the supernatant was color-free. The bead suspension was then equilibrated with PBS and stored in the refrigerator at 4° C.

Preparation of ALEXA633-Con-A/Alkali Blue 6B-SEPHADEX

A small volume of a wet suspension of Alkali Blue 6B-SEPHADEX (0.7 mL) was pipetted into a 1 mL pipette tip the outlet of which was blocked with a small piece of filter paper to prevent the beads from passing through. After the bead suspension settled, 1 mL of 10 mg ALEXA633 Con A was passed through the column which was then rinsed with one column volume of PBS buffer. The suspension was then transferred to a 1.5 mL tube. The tube was frozen at −20° C. for 60 min and subsequently freeze-dried. The blue powder was stored at 4° C. until further use.

Example 2

Preparation of Cores with Dyed SEPHAROSE-Concanavalin-A Substrates and Glucose Modified ALEXA633-albumin Analogues Dyeing of SEPHAROSE Beads SEPHAROSE beads were dyed with Alkali Blue 6B using the divinyl procedure described above except the SEPHADEX beads were replaced with SEPHAROSE beads.

Conjugation of Alkali Blue 6B/SEPHAROSE with Concanavalin-A Using periodate-oxidation A suspension of 4 mL Alkali Blue-SEPHAROSE was washed in distilled water. Then 50 mg of NaIO$_4$ dissolved in 1 mL of distilled water was slowly added to the suspension. The suspension was gently shaken and incubated for 60 minutes. The oxidation reaction was halted by adding 2 mL of 2 M ethylene glycol, followed by incubation for 30 min at room temperature. This activated SEPHAROSE suspension was washed several times with 10 mL of 0.01 M sodium carbonate buffer pH 9.2.

A Concanavalin-A solution was made by dissolving 100 mg of Concanavalin-A in 3 mL of a sodium carbonate buffer, containing 1 mM of calcium chloride and 50 mM of Methylmannose. This solution was added to the SEPHAROSE suspension and stirred for 12 hours at 22° C. The Concanavalin-A/conjugated Alkali Blue-SEPHAROSE was washed with phosphate buffered saline (pH 7.2) containing 1 mM of calcium chloride until the supernatant was free of Concanavalin-A.

Conjugation of Albumin with Glucose and ALEXA633

ALEXA633 was covalently linked to albumin using the ALEXA633 protein conjugation kit supplied by Molecular Probes. Five-hundred μL of sodium carbonate buffer was added to a pre-dissolved solution containing 5 mg of glucosepyranosylphenyl isothiocyanate (glucose-PITC) in 30 μL of dimethylsulfoxide. Twenty milligrams of ALEXA633-albumin was dialyzed against sodium carbonate buffer and mixed with the solution of glucose-PITC. The mixture was gently shaken and the reaction was allowed to proceed at 4° C.

for 15 hours. Glucose-modified-ALEXA633-albumin conjugate was then separated from non-reacted glucose-PITC by size exclusion chromatography using Sephadex G50.

Preparation of ALEXA633-Glucose-Albumin/Alkali Blue 6B-Concanavalin-A-SEPHAROSE

A small volume of wet suspension of Alkali Blue 6B-Con A-SEPHAROSE (0.7 mL) was pipetted into a 1 mL pipette. The tip outlet had been previously blocked with a small piece of filter paper to prevent the beads from passing through. After the bead suspension settled in the tip, 1 mL of 10 mg ALEXA633-glucose-albumin from above was passed through the column, which then was rinsed with one column volume of PBS buffer. The suspension was then transferred to a 1.5 mL tube. The tube was frozen at −20° C. for 60 min and subsequently freeze-dried. The blue powder was stored at 4° C. until further use.

Example 3

Fabrication of Glucose Sensing Capsule by Manual Deposition

Sensor cores for the devices were fabricated as follows: 50 µL drops of a deionized water solution of (1) SEPHADEX (100 mg/mL) ALKALI BLUE 6B as the binding substrate, (2) ALEXA633-Concanavalin-A (0.5 mg/L) as the labeled analogue, and (3) polyethylene glycol (100 mg/mL) as the intermediate layer were dispensed on PARAFILM. After evaporation of water, the materials formed a core approximately 1 mm in diameter. At this point, the polyethylene glycol acts to bind together the SEPHADEX and ALEXA labeled Concanavalin-A to give the core mechanical integrity.

The cores were then coated in cellulose acetate by depositing 50 µL of a 100 mg/mL solution of cellulose acetate in acetone, drying for 2-3 minutes, and then depositing 50 µL of cellulose acetate on the opposite side of the core. The resulting capsules were placed in water for conditioning overnight. The process produces a cellulose acetate membrane that is 100 microns thick and permeable to glucose. The capsule can be made smaller by depositing less volume in the sensor core. The 1 mm packet can be implanted with a small incision thus reducing the chances of infection.

Example 4

Fabrication of a Glucose Sensing Capsule Using Spray Drying

A mixture of (1) SEPHADEX (100 mg/mL) ALKALI BLUE 6B as the carrier bead, (2) ALEXA633-Concanavalin-A (0.5 mg/l) as the labeled analyte, and (3) polyethylene glycol (100 mg/mL) as the inert material in deionized water were spray dried in air to form particles 5-10 µm in diameter. The particles were then dispersed into a 50 mg/mL solution of cellulose acetate in acetone. The dispersion was sprayed again to coat the core particles with cellulose acetate. The cellulose acetate capsules were conditioned overnight as in Example 1.

Example 5

Fabrication of a Glucose Sensing Capsule by Emulsion

A mixture of (1) SEPHADEX (100 mg/mL) ALKALI BLUE 6B as the carrier bead, (2) ALEXA633-Concanavalin-A (0.5 mg/l) as the labeled analogue, and (3) polyethylene glycol (100 mg/mL) as the intermediate layer in deionized water was dispersed in a solution of cellulose acetate in methylene chloride as the continuous phase to form a water-in-oil emulsion. The dispersion was stirred vigorously and isopropanol was added to remove the water leaving the core particles suspended in methylene chloride. The suspension was then poured in a large excess (10:1) of water with 1% polyvinyl alcohol as the emulsifier and stirred until the methylene chloride evaporated. The cellulose acetate coated capsules were collected and conditioned in water as above. Using this process, capsules in the 0.5µm-5 µm range are fabricated.

Example 6

Fabrication of a Glucose Sensing Capsule by Film Encapsulation of Multiple Cores Smaller cores were prepared by forming a dispersion from SEPHADEX ALKALI BLUE 6B (91 mg), polyethylene glycol (1500 MW) (91 mg), ALEXA633-Concanavalin-A (0.14 mg/mL), and deionized water (1 mL). Larger cores are prepared from a dispersion of SEPHADEX ALKALI BLUE(101 mg), polyethylene glycol (1 to 1 mixture of 600 and 1500 g/mole) (101 mg), ALEXA633-Concanavalin-A (0.14 mg/mL), and deionized water (1 mL). Either dispersion was dispensed on a release sheet of PARAFILM in 5 µL droplets and allowed to dry. The smaller cores have a diameter in the 500 µm range, while the larger cores are in the 1000 µm range.

Figure 3:
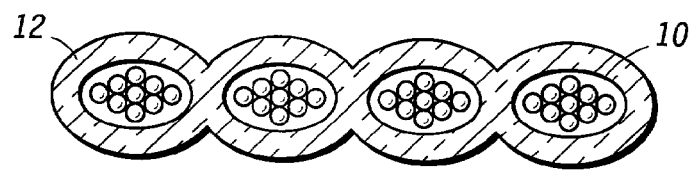
FIG. 3 illustrates a device having multiple individual cores (10) fully encapsulated in a cellulose acetate film (12).

The cores were then dispersed in 100 µL of cellulose acetate solution (10% by weight in acetone). This dispersion was cast into a thin film so the core particles were about 1 layer thick and allowed to dry. The film forms a structure with many individual cores fully encapsulated in the cellulose acetate membrane material as shown in FIG. 3. The film was on the order of 50 µm thick. The SEPHADEX/PEG compartments were on the order of 600 µm thick for the smaller cores and on the order of 1000 µm thick for the larger cores. The films were then conditioned to remove the PEG, thereby creating a void volume.

It should be noted that it is foreseeable to use immobilized cores in any of the preceding examples by mixing the core components with a cross-linked polyacrylamide or other binder before encapsulation.

Example 7

Fabrication of a Glucose Sensing Capsule by Film Encapsulation of Immobilized Cores An immobilized core film was prepared by forming a dispersion from SEPHADEX (91 mg), polyethylene glycol (1500 MW) (91 mg), ALEXA633-Concanavalin-A (0.14 mg/mL), polyacrylamide binder dyed with alkali blue (100 mg), and deionized water (2 mL). The dispersion was cast into a thin film, approximately 100 µm thick, onto a release sheet of PARAFILM and allowed to dry. The film was then removed and cut into approximately 3 mm diameter sections.

Figure 4:
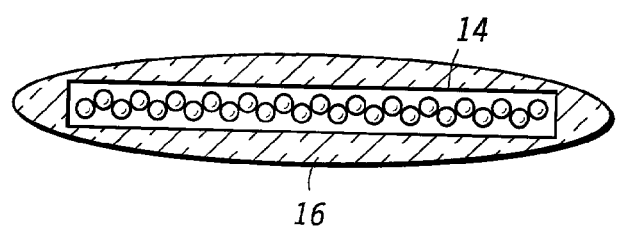
FIG. 4 illustrates a device with multiple SEPHADEX binding substrates immobilized in a binder to form a single core (14) that is fully encapsulated in a cellulose acetate film (16).
Figure 5:
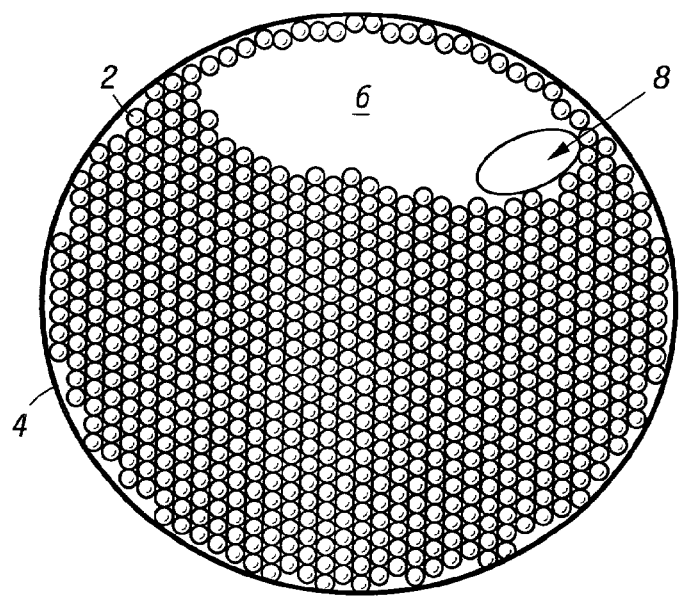
FIG. 5 illustrates an analyte-sensing device in accordance with an embodiment of the present invention, wherein a void volume (6) is internal to the binding substrate layer (2). The binding substrate layer (2) is surrounded by an analyte-permeable membrane (4). The device can also contain a reference (8).

The film sections were then dip coated with cellulose acetate solution (10% in acetone) and allowed to dry. When dry, the capsules had a total thickness on the order of 200 µm and a diameter on the order of 3 mm. The cellulose acetate membrane completely encapsulated the core, as shown in FIG. 4, and had a thickness of 100 µm.

The invention claimed is:
1. A device for detecting the presence of an analyte in a sample, comprising:
  (a) a core comprising:
    (i) a binding substrate comprising a binding site within a porous material, wherein the binding site comprises a molecular imprint of the analyte
    (ii) at least one analogue that binds in the binding site and that has a label with a first emission wavelength;
    (iii) a quenching dye located within the porous material of the binding substrate; and
    (iv) a void volume that is at least partially defined by the binding substrate;
  (b) a reference with a different emission wavelength than the label; and
  (c) an analyte-permeable membrane that completely encapsulates components (a) and (b) and that is transparent to light of the wavelengths that excite the label and the reference, wherein the device is seamless and wherein the analogue is capable of flowing in and out of the porous material into the void volume, while the quenching dye is not capable of leaving the porous material.
2. The device of claim 1, wherein said quenching dye absorbs said first emission wavelength.
3. The device of claim 1, wherein said quenching dye absorbs an excitation wavelength.
4. The device of claim 1, wherein said analyte-permeable membrane is treated with a biocompatibility enhancer selected from the group consisting of polyethylene glycol, polysilicones, parylene, and angiogenic materials.
5. The device of claim 1, wherein said reference is covalently bonded to the interior of the analyte-permeable membrane.
6. The device of claim 1, wherein said reference is in the analyte-permeable membrane.
7. The device of claim 1, wherein said reference is in the void volume.
8. The device of claim 1, wherein said reference is in the core.
9. The device of claim 1, wherein the binding substrate has an inherent affinity for the analyte.
10. The device of claim 1, wherein a molecule having an affinity for the analyte is linked to the binding substrate.
11. The device of claim 1, wherein said binding substrate further comprises a material selected from the group consisting of dextrans, glycogens, yeast mannans, amylopectins, levans, globulin, proteins, hormones, antibodies, thyroxin binding globulin, actin, and tubulin.
12. The device of claim 1, wherein the binding substrate comprises crosslinked dextran.
13. The device of claim 1, wherein the binding substrate is immobilized in a binder.
14. The device of claim 13, wherein said binder is selected from the group consisting of hydrogels, silicone containing polymers, polysulfones, polyacrylamides, epoxies, and combinations thereof.
15. The device of claim 13, wherein said binder is cross-linked polyacrylamide.
16. The device of claim 1, wherein the void volume surrounds the binding substrate.
17. The device of claim 1, wherein the binding substrate surrounds at least part of the void volume.
18. The device of claim 1, wherein the analogue is a glucose analogue.
19. The device of claim 1, wherein said analogue is selected from the group consisting of lectins, Concanavalin-A, wheat germ agglutinin, and soybean agglutinin.
20. The device of claim 1, wherein the analogue is Concanavalin-A.
21. The device of claim 1, wherein said label is an organic dye.
22. The device of claim 1, wherein said label has an excitation wavelength of 633 nm and an emission wavelength of 647 nm.
23. The device of claim 1, wherein said label is covalently bonded to said analogue.
24. The device of claim 1, wherein the reference is a quantum dot.
25. The device of claim 1, wherein the reference is an organic dye.
26. The device of claim 1, wherein said reference is selected from the group consisting of cyanine dyes and phycobiliproteins.
27. The device of claim 1, wherein said analyte-permeable membrane is selected from the group consisting of cellulose acetate, polysulfones (UDEL), polycarbonates, poly(vinyl chlorides), polyaimides, ethylene vinyl acetate copolymers, poly(vinylidene) fluoride, poly(urethanes), poly(benzimidazoles), cellulose esters, cellulose triacetate, cellulose, cellulose nitrate, regenerated cellulose, cross-linked poly(vinylpyrrolidone), cross-linked polyacrylamide, cross-linked poly(hydroxy ethyl methacrylate), polyurethanes, polyureas, hydrogels, silicon-containing polymers, polyethers, acrylics, P-HEMA, nafion, and glutaraldehyde, or mixtures thereof.
28. The device of claim 1, wherein the analyte-permeable membrane is made from at least one of cellulose acetate or a polysulfone.
29. The device of claim 1, wherein the analyte-permeable membrane is made from cellulose acetate.
30. The device of claim 1, wherein said analyte-permeable membrane further comprises magnetic or metallic particles.
31. The device of claim 1, wherein said analyte is selected from the group consisting of glucose, thyroxin, coumadin, synthroid, cyclosporin, erythropoietin, lopid, monopril, digoxin, amiodarone, prothrombin, cytokines, chemokines, creatinine, lactate, taxol, and fluorouracil.
32. The device of claim 1, wherein said analyte is glucose.
33. The device of claim 1, wherein a ratio of the void volume to a volume occupied by the binding substrate is between about 0.05 and about 5, inclusive.
34. The device of claim 33, wherein the ratio is between about 0.5 and about 3, inclusive.
35. The device of claim 33, wherein the ratio is about 1.
36. The device of claim 1, wherein a weight ratio of the analogue to the binding substrate is about 0.1 to about 10.
37. A method of detecting the presence of one or more analytes in a sample in vivo, comprising:
  I. implanting in the skin of a living organism, in fluid contact with a biological fluid, a device for detecting the presence of an analyte in a sample, the device comprising:
    (a) a core comprising
      (i) a binding substrate comprising a binding site within a porous material, wherein the binding site comprises a molecular imprint of the analyte
      (ii) at least one analogue that binds in the binding site and that has a label with a first emission wavelength;
      (iii) a quenching dye located within the porous material of the binding substrate; and
      (iv) a void volume that is at least partially defined by the binding substrate;
    (b) a reference with a different emission wavelength than the label; and

(c) an analyte-permeable membrane that completely encapsulates components (a) and (b) and that is transparent to light of the wavelengths that excite the label and the reference,
wherein the device is seamless and
wherein the analogue is capable of flowing in and out of the porous material into the void volume, while the quenching dye is not capable of leaving the porous material;

II. irradiating the device with light; and

III. detecting light emitted from the device.

38. The method of claim 37, wherein irradiating is performed with a laser.

39. The method of claim 37, wherein irradiating is performed with a laser that emits in the infrared band.

* * * * *